United States Patent
Aramata et al.

(12)

(10) Patent No.: US 6,218,562 B1
(45) Date of Patent: Apr. 17, 2001

(54) PROCESS FOR PREPARING ORGANOHALOSILANES

(75) Inventors: Mikio Aramata; Akio Ohori; Masaaki Furuya; Susumu Ueno; Toshio Shinohara; Tetsuya Inukai, all of Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/548,053

(22) Filed: Apr. 12, 2000

(51) Int. Cl.$^7$ .................................................. C07F 7/16
(52) U.S. Cl. ............................................... 556/472
(58) Field of Search .............................. 556/472

(56) References Cited

U.S. PATENT DOCUMENTS

| 5,334,738 | 8/1994 | Pachaly et al. |
| 5,783,721 | * 7/1998 | Tsumura et al. ..................... 556/472 |
| 6,090,966 | * 7/2000 | Nakanishi et al. ................... 556/472 |

FOREIGN PATENT DOCUMENTS 6-234776   8/1994   (JP) .

OTHER PUBLICATIONS

*Refining and Characterization of Silicon for the Chemical Industry* Silicon for the Chemical IndustryIV: Geirenger, Norway, Jun. 3–5, 1998 pp. 51–68 Neto et al.

*Method for the Determination of Active Aluminium in Silicon*–Proceeding Silicon for the Chemical IndustryIV, 1998 Jun. 3–5 pp. 69–74 Eie et al.

*The Influence of Surface Oxygen in the Rochow Direct Process* –Silicon for the Chemical Industry, Geirenger, Norway 1992 pp. 85–98 Hutchings et al.

*Influence of Oxygen Pollution of Silicon Metal in the Rochow Synthesis* –Silicon for the Chemical Industry II, Leon, Norway, 1994 pp. 121–127 Laroze, G.

J. Catal. Vol. 159, 1996, pp. 31–41 *Effect of Silicon Dioxide Thickness on the Direct Synthesis of Dimethyldichlorosilane;* Yilmaz et al.

* cited by examiner

Primary Examiner—Paul F. Shaver
(74) Attorney, Agent, or Firm—Millen, White, Zelano & Branigan, P.C.

(57) ABSTRACT

Organohalosilanes are prepared by the Rochow process of reacting metallic silicon particles with an organohalide in the presence of a copper catalyst. The metallic silicon particles, which are prepared by comminuting fragments of metallic silicon raw material, have a mean particle size of 10 $\mu$m to 10 mm and a surface oxygen quantity of up to 0.3 wt % which is given as the difference between the oxygen concentrations determined by in-metal oxygen analysis of the metallic silicon particles and the fragments, respectively.

9 Claims, 1 Drawing Sheet

PROCESS FOR PREPARING ORGANOHALOSILANES

This invention relates to a process for preparing organohalosilanes by the so-called Rochow reaction.

BACKGROUND OF THE INVENTION

The Rochow reaction is typically employed in the industrial process for the synthesis of organohalosilanes such as methylchlorosilanes. The Rochow reaction is the direct reaction of organic halides such as alkyl halides and phenyl halides with metallic silicon particles which is carried out at 250 to 500° C. in the presence of a copper catalyst and a co-catalyst. While this reaction requires keeping a high reaction rate, a key technology in the synthesis of methylchlorosilanes is to increase the selectivity of the most desirable dimethyldichlorosilane. A key technology in the synthesis of phenylsilanes is to produce the desirable diphenyldichlorosilane and phenyltrichlorosilane in a composition matching with their demand.

The conventional Rochow reaction requires a very long time for activation until the reaction reaches a steady state. The steady state, in turn, is relatively short. The contact mass's activity lowers with the lapse of time, and the yield of diorganodichlorosilane decreases accordingly. In the synthesis of methylsilanes, for example, there arise problems that high-boiling fractions such as disilanes and undesired products such as methyltrichlorosilane increase due to side reaction. This necessitates exchanging the contact mass in the reactor. Shortening the activation time is one of the outstanding problems. Since the Rochow reaction mainly uses reaction in a fluidized bed or agitating fluidized bed, a variety of reports have been made on the particle size of metallic silicon particles suitable to form the fluidized bed.

In this reaction, it is important to increase the reaction rate of metallic silicon because the cost of metallic silicon is predominant among the raw material cost. Since a variety of by-products usually form in addition to the desired diorganodichlorosilane, it is also important to control reaction conditions so that the proportion of these by-products may comply with the supply/demand balance of organochlorosilanes. Industrially, this reaction is generally carried out in a reactor such as a fluidized bed, vibrating fluidized bed or agitating fluidized bed while replenishing the contact mass to the reaction system. The reaction is a very complex gas-solid heterogeneous reaction in that the reaction itself occurs on surfaces of metallic silicon particles and the catalyst is solid. For this reason, the reaction mechanism has not been well understood. It is empirically known that the results of reaction vary over a wide range depending on the attributes (including source, manufacturer, manufacturing equipment, and crushing technique) of particular metallic silicon particles used. Several proposals have been made in this regard, but none of them have become established. In the present status, when metallic silicon of a new lot or origin becomes available, a preliminary reaction test must be done to determine whether or not it can be used in practice. Since many factors of metallic silicon that affect the reaction have not yet been revealed, lively discussions have recently been made in the society of metallic silicon (see, for example, Silicon for the Chemical Industry IV: Geirenger, Norway, Jun. 3–5, 1998).

What is important is the reaction activity of metallic silicon particles subject to reaction. The reaction activity has been studied from various aspects. In this regard, a variety of proposals (for example, relating to properties of metallic silicon itself) have been made. More specifically, it is well known that aluminum which is present in metallic silicon as an impurity is effective as a co-catalyst for the Rochow reaction. Aluminum at the same level is active in some form, but inactive in other form. For the reason that only the active form of aluminum present in metallic silicon as an impurity is necessary, H. M. Rong et al. reported the method of measuring active aluminum and recommended the use of active aluminum (see Proceeding Silicon for the Chemical Industry, pp. 69 (1998)). U.S. Pat. No. 5,334,738 or JP-A 6-234776 discloses a method for quantitatively determining the dispersion of intermetallic compounds in metallic silicon as an impurity and the criterion of choice of metallic silicon for reactivity control. This method involves cutting a metallic silicon mass, polishing the surface to a mirror finish, observing the morphology of the surface under a microscope, and computing a structural parameter QF from structural factors. Metallic silicon having the structural parameter QF of 18 to 60 has the highest reactivity and its use is recommended. U.S. Pat. No. 5,281,739 discloses to evaluate the reactivity of a contact mass by adding copper to molten metallic silicon.

Making follow-up tests on these methods, we found that the reactivity of metallic silicon could not be determined by any of these methods while these methods were effective only in special limited systems. These methods cannot be universally adopted.

In general, metallic silicon remains stable in that it has been oxidized on its surface and is covered with stable silicon oxide so that inward oxidation may not proceed beyond a certain thickness. However, as seen from the semiconductor silicon, it is well known that silicon itself has a very high oxidizing ability and there is not available metallic silicon which is free of oxide film in air. It is also known that the surface of metallic silicon particles for use in the Rochow reaction has more or less oxide film, which affects the Rochow reaction. The oxide film on metallic silicon relative to reactivity and selectivity in methylsilane reaction is discussed in the reports of G. J. Hutching et al., Silicon for the Chemical Industry, Geirenger, Norway, pp. 85–98, 1992, and G. Laroze, Silicon for the Chemical Industry II, Leon, Norway, pp. 121–127, 1994. These reports describe the influence of oxide film on reactivity and selectivity while the oxide film on metallic silicon particles is locally analyzed by x-ray photoelectron spectroscopy. Also, J. L. Falconer et al., J. Catal., vol. 159, pp. 31–41, 1996, study an oxide film on a silicon wafer and discuss the orientation of crystals and reactivity. This discussion is not applicable to the surface of metallic silicon particles for the Rochow reaction. None of the foregoing reports establish a measurement method for specifying metallic silicon particles for industrial use.

As understood from the above, the heretofore proposed methods are not generally applicable to the industrial use. When the Rochow reaction was actually carried out using metallic silicon particles which were selected under any of the foregoing selection criteria while the remaining factors are set identical, the results of reaction experienced a wide range of variation. Therefore, metallic silicon particles having properties specified by any of the prior art proposals are applicable to only a special reaction system. There is a need to have metallic silicon particles capable of finding practical use in the industry and their evaluation method.

SUMMARY OF THE INVENTION

An object of the invention is to provide a process for preparing organohalosilanes, capable of facilitating and ensuring the selection of active metallic silicon particles used in the Rochow reaction.

We have found that the activity of metallic silicon particles used in the Rochow reaction is closely correlated to the thickness and quantity of oxide film formed on metallic silicon surface which can be measured as a surface oxygen quantity. For the measurement of the surface oxygen quantity, metallic silicon particles and fragments of metallic silicon raw material which are to be comminuted into the metallic silicon particles are separately measured for oxygen concentration by in-metal oxygen analysis (oxygen fractionation using an inert gas fusion furnace), the surface oxygen quantity being given by the difference between these oxygen concentrations. Metallic silicon particles having a surface oxygen quantity thus determined to be up to 0.3% by weight are selected for use in the reaction. This method ensures to select metallic silicon particles having a high activity necessary for the synthesis of organohalosilanes by the direction reaction of organic halides with metallic silicon powder. This enables to reduce the activation time of the contact mass taken until the steady state is reached, also known as the triggering of reaction, which has been a bottle neck in the Rochow reaction, improve the selectivity in the steady state even when the rate of reaction is increased, and as a result, increase the percent effective utilization of silicon. In one prior art procedure relating to metallic silicon, a preliminary reaction test using comminuted metallic silicon particles is performed for evaluating the reaction activity thereof before the industrial use of metallic silicon particles is decided. The present invention solves the problem of such an extra test.

The invention provides a process for preparing organohalosilanes comprising reacting metallic silicon particles with an organohalide in the presence of a copper catalyst. The metallic silicon particles, which are prepared by comminuting fragments of metallic silicon raw material, have a mean particle size of 10 μm to 10 mm and a surface oxygen quantity of up to 0.3% by weight which is given as the difference between the oxygen concentrations determined by in-metal oxygen analysis of the metallic silicon particles and the fragments, respectively. It is recommended to select for use in the process metallic silicon particles having an oxygen content of up to 0.01 g per square meter of silicon surface area.

In the prior art relating to the organochlorosilane synthesizing reaction (known as the Rochow reaction) between an alkyl halide (e.g., methyl chloride) or aryl halide (e.g., benzene chloride) and metallic silicon in the presence of a copper catalyst and co-catalyst, the outstanding problems are the activation time (or induction period) taken long until the steady state is reached as well as the reaction rate and selectivity to form silanes. To solve these problems, an improvement in catalyst composition and an improvement in metallic silicon particles themselves are necessary. We have learned the mechanism of silane reaction and succeeded in optimizing metallic silicon particles, thereby solving the above-mentioned problems of the Rochow reaction. It becomes possible to increase the selectivity of the desired diorganodihalosilane and improve the yields of reaction products. It also becomes possible to exclude the preliminary reaction test suffering from a wide range of variation and manage the Rochow reaction in a quantitative manner.

BRIEF DESCRIPTION OF THE DRAWINGS

The only figure, FIG. 1 schematically illustrates a system for the preparation of organohalosilanes.

DESCRIPTION OF THE PREFERRED EMBODIMENTS

Figure 1:
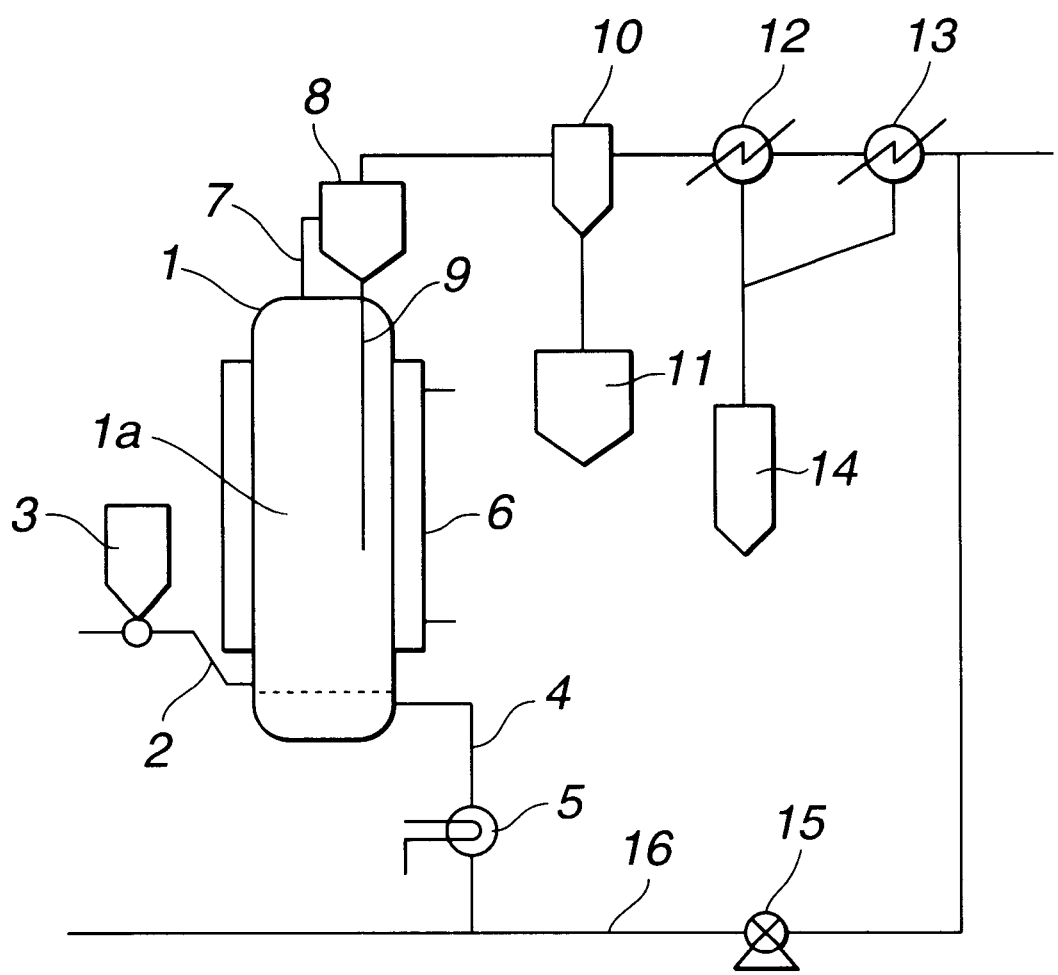

The invention is directed to a process of contacting an organohalide (e.g., alkyl halide or aryl halide) with metallic silicon particles in the presence of a copper catalyst to form organohalosilanes of the following formula:

$$R_m H_n SiX_{4-m-n} \quad (1)$$

wherein R is $C_{1-4}$ alkyl or aryl such as phenyl, X is a halogen atom such as chlorine or bromine, and "m" is an integer of 1, 2 or 3, "n" is an integer of 0, 1 or 2, and m+n is an integer of up to 4. In particular, the invention places a focus on the metallic silicon particles used in this Rochow reaction. Therefore, the invention pertains to the selection of metallic silicon particles which can reduce the activation time (or induction period) taken until the reaction reaches a steady state, that has been a bottle neck in reaction of this sort, and sustain the high activity in the steady state, to the method of evaluating the activity, and to the use of metallic silicon particles in the Rochow reaction.

More particularly, metallic silicon is usually prepared by reducing silica along with carbon in an arc furnace at a high temperature above 2,500° C., which requires a large amount of electric energy and naturally adds to the cost of silicon. The cost of organohalosilane which is a precursor to silicone resin largely depends on the conversion rate of the expensive metallic silicon to the silane (because a variety of silane by-products form due to side reaction), the production rate (or selectivity) of useful silanes meeting the demand balance, and the reaction rate which is considered important for the industrial process. From such a standpoint, silicone manufacturers use the simple term "reactivity" for both the selectivity and reaction rate of the product and seek for metallic silicon capable of exhibiting a high reactivity in their own manufacturing apparatus. On the other hand, regarding metallic silicon for use in the Rochow reaction and the manufacture of trichlorosilane as a semiconductor raw material approximate to the Rochow reaction (the majority of the overall consumption of metallic silicon is used in these industrial areas), metallic silicon manufacturers actually perform a simulation of the reaction and make from their own aspect research for forming metallic silicon having a high reactivity and selectivity while paying attention to the content and form of impurities, manufacturing method, cooling method, etc. The fruitful results of such research about metallic silicon for chemical use are reported in the international meeting "Silicon for Chemical Industry" held in Norway at intervals of every two years where information exchange is made. Since the Rochow reaction itself is not thoroughly understood up to the present, each manufacturer makes the evaluation of metallic silicon based on its own scale.

The Rochow reaction is a gas-solid heterogeneous reaction between the organic halide which is gaseous at elevated temperature and metallic silicon which is solid even at elevated temperature in the presence of a catalyst. Since it is expected that the reactivity largely depends on the nature of metallic silicon as crystal, the method for quantitatively determining the dispersion of intermetallic compounds as impurities in metallic silicon and the criterion of choosing metallic silicon for reactivity control proposed in JP-A 6-234776 are reasonable at a glance and worth considering. This method involves cutting a metallic silicon mass, polishing the surface to a mirror finish, observing the metallurgical state of the surface under a microscope, and computing a structural parameter QF from structural factors. The use of metallic silicon having the structural parameter QF of 18 to 60 is recommended because of the highest reactivity.

However, making analysis on the size of crystallites in ordinary metallic silicon of industrial grade, we found that crystallites in ordinary metallic silicon of industrial grade are of millimeter order because silicon is highly crystalline. By contrast, metallic silicon particles used in actual reaction have a size of about 100 microns at most. It is then evident that metallic silicon particles used in the Rochow reaction each consist of a few crystallites. It is thus believed that the state of intermetallic compounds in metallic silicon as impurities observed under a microscope does not always represent the crystallinity of metallic silicon that governs reactivity.

Since crystal defects are present in these zones, comminution of metallic silicon causes impurity-containing areas to selectively develop at surfaces. The active aluminum theory proposed by H. M. Rong et al., Proceeding Silicon for the Chemical Industry, pp. 69, 1998, is considered, based on its measurement method (measured in terms of the quantity extracted with aqueous hydrochloric acid), to indicate that aluminum present on surfaces of metallic silicon particles is active. However, these areas selectively develop at surfaces as a result of comminution, the extracted quantity is proportional to the amount of aluminum, and the percent extraction is substantially constant. The method of H. M. Rong et al. cannot be directly applied to the relevant reaction.

As described above, the Rochow reaction is a gas-solid heterogeneous reaction between the organic halide which is gaseous at elevated temperature and metallic silicon particles which remain solid even at elevated temperature. As understood from the reports of G. Laroze, Silicon for the Chemical Industry II, Leon, Norway, pp. 121–127, 1994 and J. L. Falconer et al., J. Catal., vol. 159, pp. 31–41, 1996, it is fully anticipated that reactivity is largely affected by the crystal orientation of metallic silicon particles and the surface state of oxide film, etc. However, a precise study of the Falconer report reveals that only the oxide film on metallic silicon and the selectivity in methylsilane reaction are discussed using semiconductor silicon. This theory is applicable with difficulty to metallic silicon particles for actual use in the industry. In the Laroze report, a specific measurement method is not referred to.

Since silicon is highly reactive in air, an oxide film forms on the surface of metallic silicon as a result of contact with air. In general, comminution, transportation and storage of metallic silicon mass are performed in an inert gas or in an atmosphere having a low oxygen concentration in order to avoid the danger of dust explosion. Since oxygen is not always completely shielded, an oxide film normally exists on the surface of metallic silicon. It is also empirically known that the reactivity of metallic silicon differs with storage conditions.

On the other hand, the process of manufacturing metallic silicon for industrial use involves, for the purpose of reducing impurities such as aluminum and calcium, the refining step of tapping silicon material into a tapping container known as ladle, and blowing oxygen or air into the molten silicon material from below, to convert the impurities into oxides for removal. In this step, silicon is also somewhat oxidized. Since the silicon monoxide thus formed has a high vapor pressure and silicon is highly crystalline as previously mentioned, silicon oxide (including silicon monoxide and dioxide) is excluded as slag upon cooling entailing crystal growth. Then little oxygen is present in metallic silicon.

It has thus been found that the majority of oxygen measured by oxygen analysis on metallic silicon particles in an inert gas fusion furnace is attributable to oxygen present on surfaces thereof (see Table 1). Since fine particulates of slag can, of course, be internally included depending on the manufacturing process, the absence of such slag particulates must be confirmed before analysis.

Through the foregoing investigations, we have found that provided that metallic silicon particles are prepared by comminuting fragments of metallic silicon raw material, the quantity of surface oxygen on metallic silicon particles is represented by the difference between the oxygen quantities of the metallic silicon particles and the fragments which are measured by means of an inert gas fusion furnace-built-in oxygen analyzer (generally known as an in-metal oxygen analyzer and commercially available as model EMGA-650 from Horiba Ltd.). We have further found that the surface oxygen quantity is divided by the surface area of metallic silicon particles to calculate an oxygen quantity per unit surface area, which becomes a useful parameter.

The samples are described in more detail. Since metallic silicon particles are highly oxidative, a sample is taken in an inert gas stream, and typically, sampling and subsequent handling for measurement are carried out in a glove box filled with an inert gas. Placement of the sample in the instrument should also be completed as quickly as possible to avoid contact with air. The fragments of metallic silicon raw material are obtained by crushing a metallic silicon mass into fragments, and collecting fragments with a weight of 20 to 100 mg, which are measured for oxygen quantity without treatment. By computing the difference between the oxygen quantities of the metallic silicon particles and the fragments, the quantity of surface oxygen on metallic silicon particles which are actually subject to the Rochow reaction is determined.

The feature of the present invention is to select metallic silicon by measuring the quantity of oxide film on surfaces of metallic silicon particles. Comparing the surface oxygen quantities on various metallic silicon specimens, we have found that metallic silicon particles must have a mean particle size of 10 microns to 10 mm and a surface oxygen quantity of up to 0.3% by weight as measured by the above-specified procedure, and preferably an oxygen content of up to 0.01 g per square meter of silicon surface area. Differently stated, the procedure involving separately measuring the oxygen quantities present on metallic silicon particles and fragments as their source by in-metal oxygen analysis (oxygen analysis in an inert gas fusion furnace) and computing the difference therebetween to give the surface oxygen quantity is appropriate for the evaluation of metallic silicon particles. This eliminates a need for a preliminary reaction test on metallic silicon particles and enables quantitative management of the reaction.

According to the invention, a choice is made of metallic silicon particles having a surface oxygen quantity of up to 0.3% by weight, preferably up to 0.25% by weight, and more preferably up to 0.2% by weight, as measured by the above-specified procedure. The lower limit of the surface oxygen quantity is not critical. As the more preferred criterion for selecting metallic silicon particles, the metallic silicon particles should contain up to 0.01 g of oxygen per $m^2$ of silicon surface area, more preferably up to 0.005 g of oxygen/$m^2$ of silicon surface area, and most preferably less than 0.003 g of oxygen/$m^2$ of silicon surface area.

Excepting the use of the above-defined metallic silicon particles, the organohalosilane preparing process of the invention may be carried out by employing any well-known procedure and conditions. For example, the copper catalyst and co-catalyst may be selected from well-known ones. The organic halide used may be selected from alkyl halides and aryl halides having an alkyl or aryl group corresponding to a desired organohalosilane, for example, methyl chloride, ethyl chloride, and phenyl chloride. According to the invention, organohalosilanes of the above formula (1), especially diorganodihalosilanes wherein m=2 and n=0, can be produced in high yields.

The amount of the copper catalyst added may be about 0.1 to about 10 parts by weight per 100 parts by weight of the metallic silicon. Any of well-known co-catalysts may be added to the copper catalyst.

FIG. 1 illustrates a system for preparing organohalosilanes. The system includes a fluidized bed reactor 1 and a reactant source tank 3 connected to the bottom of the reactor 1 through a reactant feed conduit 2, whereby metallic silicon and a copper catalyst or a mixture of a copper catalyst and a co-catalyst are admitted into the bottom of the reactor 1. A conduit 4 for the other reactant, organic halide has a heater 5 inserted therein and is connected to the reactor 1 at the bottom. The organic halide in gas or vapor form is also introduced into the bottom of the reactor 1, thereby forming a fluidized bed 1a of the metallic silicon and the catalyst within the reactor 1. The reactor 1 is enclosed with a cooling jacket 6.

Preferably the organic halide in gas or vapor form is introduced into the reactor 1 at a linear velocity of 2 to 10 cm/sec in the steady state. Reaction is generally carried out at a temperature of 250 to 350° C.

The organohalosilane product resulting from the reaction is channeled through a discharge conduit 7 connected to the top of the reactor 1 to a first cyclone 8 where the entrained solid particles are separated and fed back to the fluidized bed 1a through a return pipe 9. The product is then fed to a second cyclone 10 where the entrained solid particles are separated and fed to a particle reservoir 11 for storage. The product is then fed to first and second silane condensers 12 and 13 where the organohalosilanes are condensed and fed to a silane reservoir 14 for storage. Part or all of the discharge gas from which solid particles have been separated and organohalosilanes have been condensed and separated is fed back to the reactor 1 through an organic halide return conduit 16 having a recycle gas compressor 15 inserted therein. The return conduit 16 is connected to the organic halide feed conduit 4.

EXAMPLE

Examples of the invention are given below by way of illustration and not by way of limitation. All parts are by weight.

Experiment

A variety of metallic silicon particles as shown in Table 1 were analyzed and evaluated for reactivity. The results are shown in Table 1.

TABLE 1

| Metallic silicon sample | | Australia produce | Australia produce | China produce | Canada produce |
|---|---|---|---|---|---|
| Reactivity rating*1 | | Active | Active | Less active | Less active |
| Total Fe (%) | | 0.17 | 0.17 | 0.20 | 0.62 |
| Total Ca (%) | | 0.02 | 0.01 | 0.04 | 0.05 |
| Total Al (%) | | 0.13 | 0.06 | 0.05 | 0.15 |
| Active Al (ppm)*2 | as is | 500 | 220 | 170 | 600 |
|  | 325# on | 760 | 290 | 260 | 650 |
| Oxygen in powder (wt %) | | 0.13 | 0.13 | 0.16 | 0.24 |
| Oxygen in fragments (wt %) | | <0.01 | <0.01 | <0.01 | <0.01 |
| Surface oxygen quantity (wt %) | | 0.13 | 0.13 | 0.16 | 0.24 |

*1 After comminution, silicon particles were stored in air and tested in a small reactor in the system of FIG. 1. Silicon was rated "Active" when it was highly active and "Less active" when it was less active than the former.
*2 Active aluminum was measured by the method of H. M. Rong et al., Proceeding Silicon for the Chemical Industry, pp. 69, 1998.

Example 1

Using a system as shown in FIG. 1, methylchlorosilanes were prepared. A steel reactor of 8 cm in diameter equipped with a spiral agitator was charged with 100 parts of each of metallic silicon powders of different produces having a mean particle size of about 50 μm which had been stored in air after comminution as shown in Table 2. With stirring by the spiral agitator, nitrogen gas was introduced into the reactor at a linear velocity of 2 cm/sec to fluidize the silicon powder while the powder was heated to 280° C. Thereafter, 3 parts of a catalyst mixture was added to the reactor. The catalyst mixture consisted of a copper catalyst in the form of a flake copper foil powder obtained by stamping, having an air-permeability method specific surface area of 0.80 m$^2$/g, a mean particle size of 47 μm. and a bulk specific gravity of 1.9 g/cm$^3$ and a co-catalyst composed mainly of antimony, brass and bronze. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. After 6 hours, the reaction was stopped. The average rate of silane production, percent consumption of metallic silicon, and the composition of the formed silanes are shown in Table 3.

For comparison purposes, using metallic silicon particles whose surface oxygen quantity had been increased by increasing contact with air during comminution, reaction was carried out under the same conditions as in Example 1. The results are also shown in Table 3.

TABLE 2

| Metallic silicon | Fe (%) | Al (%) | Ca (%) | BET specific surface area (m²/g) | Oxygen in powder (wt %) | Oxygen in fragments (wt %) | Surface oxygen quantity (wt %) | Surface oxygen content (g/m²) |
|---|---|---|---|---|---|---|---|---|
| Example | | | | | | | | |
| AS-1 Australia produce | 0.13 | 0.05 | 0.01 | 0.56 | 0.13 | <0.01 | 0.13 | 0.0023 |
| AS-2 Australia produce | 0.15 | 0.06 | 0.02 | 0.60 | 0.15 | <0.01 | 0.15 | 0.0025 |
| AS-3 Australia produce | 0.18 | 0.11 | 0.02 | 0.61 | 0.13 | <0.01 | 0.13 | 0.0021 |
| AS-4 Australia produce | 0.24 | 0.16 | 0.01 | 0.58 | 0.10 | <0.01 | 0.10 | 0.0017 |
| BS China produce | 0.20 | 0.05 | 0.05 | 0.65 | 0.19 | <0.01 | 0.19 | 0.0026 |
| CS Canada produce | 0.32 | 0.16 | 0.05 | 0.53 | 0.23 | <0.01 | 0.23 | 0.0043 |
| DS Norway produce | 0.29 | 0.05 | 0.03 | 0.64 | 0.19 | <0.01 | 0.19 | 0.0030 |
| BS-1 South America produce | 0.25 | 0.09 | 0.03 | 0.60 | 0.24 | <0.01 | 0.24 | 0.0040 |
| BS-2 South America produce | 0.27 | 0.17 | 0.03 | 0.52 | 0.21 | <0.01 | 0.21 | 0.0040 |
| BS-3 South America produce | 0.29 | 0.20 | 0.03 | 0.63 | 0.30 | 0.07 | 0.23 | 0.0048 |
| Comparative Example | | | | | | | | |
| AS-10 | 0.13 | 0.05 | 0.01 | 0.85 | 0.43 | <0.01 | 0.43 | 0.0051 |
| AS-30 | 0.24 | 0.16 | 0.01 | 0.75 | 0.36 | <0.01 | 0.36 | 0.0048 |

Note: The surface oxygen quantity is the oxygen quantity in powder minus the oxygen quantity in fragments.

AS-10 and AS-30 were obtained by comminuting Australia produce silicon samples AS-1 and AS-3 in an oxygen atmosphere, respectively.

TABLE 3

| Metallic silicon | Surface oxygen quantity (wt %) | Production rate (g/100 g − Si · hr) | Me(H)SiCl₂ (%) | Me₂SiCl₂ (%) | MeSiCl₃ /Me₂SiCl₂ ratio |
|---|---|---|---|---|---|
| Example | | | | | |
| AS-1 | 0.13 | 18.6 | 1.3 | 91.3 | 0.051 |
| AS-2 | 0.15 | 17.1 | 2.8 | 87.0 | 0.068 |
| AS-3 | 0.13 | 20.5 | 1.5 | 88.3 | 0.083 |
| AS-4 | 0.10 | 21.0 | 1.4 | 89.0 | 0.058 |
| BS | 0.19 | 10.1 | 3.8 | 83.2 | 0.083 |
| CS | 0.23 | 9.5 | 3.5 | 85.0 | 0.109 |
| DS | 0.19 | 10.2 | 4.5 | 82.7 | 0.111 |
| ES-1 | 0.24 | 8.8 | 4.5 | 84.2 | 0.102 |
| ES-2 | 0.21 | 10.1 | 3.3 | 84.6 | 0.102 |
| ES-3 | 0.23 | 15.6 | 4.5 | 85.8 | 0.115 |
| Comparative Example | | | | | |
| AS-10 | 0.43 | 5.0 | 5.8 | 71.2 | 0.183 |
| AS-30 | 0.36 | 4.7 | 6.1 | 70.0 | 0.153 |

There have been described metallic silicon particles with a specific parameter which are active in the Rochow reaction, effective in increasing the reaction rate, especially in the activation period, and reducing the activation period, and eventually improving the results of the Rochow reaction. The invention eliminates a need for a preliminary reaction test on metallic silicon whose results have a wide range of variation, and enables a quantitative forecast of the activity of metallic silicon particles. The invention is valuable and epoch-making in the industry in that the selection of metallic silicon particles optimum for the Rochow reaction is possible.

Japanese Patent Application No. 11-104694 is incorporated herein by reference.

Reasonable modifications and variations are possible from the foregoing disclosure without departing from either the spirit or scope of the present invention as defined by the claims.

What is claimed is:

1. A process for preparing organohalosilanes comprising reacting metallic silicon particles having a mean particle size of 10 $\mu$m to 10 mm with an organohalide in the presence of a copper catalyst, wherein
   the metallic silicon particles, which are prepared by comminuting fragments of metallic silicon raw material, have a surface oxygen quantity of up to 0.3 wt % which is given as the difference between the oxygen concentrations determined by in-metal oxygen analysis of the metallic silicon particles and the fragments, respectively.

2. The process of claim 1 wherein the metallic silicon particles have an oxygen content of up to 0.01 g per square meter of silicon surface area.

3. The process of claim 1, wherein the organohalide is alkyl halide or an aryl halide.

4. The process of claim 1, wherein the organohalide is methyl chloride, ethyl chloride or phenyl chloride.

5. The process of claim 1, wherein the metallic silicon particles have a surface oxygen quantity of up to 0.2% by weight.

6. The process of claim 1, wherein the metallic silicon particles have a surface oxygen quantity of up to 0.25% by weight.

7. The process of claim 1, wherein the metallic silicon particles have an oxygen content of up to 0.005 g per square meter of silicon surface area.

8. The process of claim 1, wherein the metallic silicon particles have an oxygen content of less than 0.003 g per square meter of silicon surface area.

9. The process of claim 1, wherein the amount of the copper catalyst is 0.1 to 10 parts per weight of the metallic silicon.

* * * * *